United States Patent [19]
Brenna et al.

[11] Patent Number: 5,661,038
[45] Date of Patent: Aug. 26, 1997

[54] INTERFACE SYSTEM FOR ISOTOPIC ANALYSIS OF HYDROGEN

[75] Inventors: J. Thomas Brenna; Herbert J. Tobias, both of Ithaca, N.Y.; Keith J. Goodman, Ames, Iowa

[73] Assignee: Cornell Research Foundation, Inc., Ithaca, N.Y.

[21] Appl. No.: 442,059

[22] Filed: May 16, 1995

[51] Int. Cl.$^6$ .......................... G01N 24/00; H01J 49/00; C01B 3/02

[52] U.S. Cl. .......................... 436/173; 250/282; 250/288; 423/648.1; 436/144; 436/145; 436/183; 422/99

[58] Field of Search .......................... 250/282, 288; 423/648.1; 436/173, 144–146, 183; 422/99

[56] References Cited

U.S. PATENT DOCUMENTS

| | | |
|---|---|---|
| 2,935,382 | 5/1960 | Osborn et al. . |
| 3,144,313 | 8/1964 | Pfefferle . |
| 3,241,293 | 3/1966 | Pfefferle . |
| 3,392,510 | 7/1968 | Koch, Jr. . |
| 3,439,474 | 4/1969 | McKinley . |
| 3,589,171 | 6/1971 | Haley . |
| 3,791,106 | 2/1974 | Haley . |
| 3,995,012 | 11/1976 | Barnert et al. . |
| 3,996,343 | 12/1976 | Bamberger et al. . |
| 4,010,249 | 3/1977 | duPont . |
| 4,490,349 | 12/1984 | Horvath . |
| 4,713,234 | 12/1987 | Weirich et al. . |
| 4,774,065 | 9/1988 | Penzhorn et al. . |
| 4,778,670 | 10/1988 | Pinto . |
| 4,849,155 | 7/1989 | Penzhorn et al. . |
| 5,012,052 | 4/1991 | Hayes .......................... 250/288 |
| 5,308,979 | 5/1994 | Villa-Aleman . |

FOREIGN PATENT DOCUMENTS

| | | |
|---|---|---|
| 507287 | 10/1992 | European Pat. Off. . |
| 1-298001 | 12/1989 | Japan . |

OTHER PUBLICATIONS

J. Bigeleisen et al. *Anal. Chem.* 1952, 24, 1356–1357.
J.R. Young et al. *Rev. Sci. Instrum.* 1960, 31, 1112–1114.
W.M. Thurston *Rev. Sci. Instrum.* 1971, 41, 963–966.
P. Thompson et al. *Proc. Int. Meet. Stable Isot.* 1980, 142–146.
J.R. Hulston et al. *N.Z.J.Sci.* 1981, 24, 313–322.
M.I Sajljad et al. *Nucleus* 1983, 31–34, 20.
W.W. Wong et al, *Mass Spectrum Rev.* 1986, 5, 313–342.
Z. Sofer et al. *Anal. Chem.* 1986, 58, 2033–2036.
W.W. Wong et al, *Am. J. Clin. Nutr.* 1987, 45, 905–913.
I. Dumke et al, *Anal. Chem.* 1989, 61, 2149–2154.
T.B. Coplen et al, *Anal. Chem*, 1991, 63, 910–912.
K.J. Goodman et al. *Anal. Chem.* 1992, 64, 1088–1095.
A.D. Morse et al, *Chem. Geol.* 1993, 107, 147–158.
J.T. Brenna *Acc. Chem. Res.* 1994, 27, 340–346.
H.J. Tobias et al. *Anal. Chem.* 1995, 67, 2486–2492.
H.J. Tobias et al. *Anal. Chem.* 1996, 68, 2281–2286.
Wong, William W., "Evaluation of a Dual Mass Spectrometer System for Rapid Simultaneous Determination of Hydrogen–2/Hydrogen–1 and Oxygen–18/Oxygen–16 Ratios in Aqueous Samples", *American Chemical Society*, 6 pgs., 1984.

*Primary Examiner*—Alren Soderquist
*Attorney, Agent, or Firm*—Jones, Tullar & Cooper, P.C.

[57] ABSTRACT

An interface system for supplying hydrogen isotopes to an isotope ratio mass spectrometer (IRMS) eliminates "memory effects" which are caused by residual water vapor being left in the interface system from a previous sample when a new sample is fed through the system. The system employs a reduction reactor for separating hydrogen isotopes from a water vapor containing sample, a water trap for removing residual water vapor from the separated hydrogen isotopes, and a Pd filter for passing only the hydrogen isotopes into a vacuum supply line for the IRMS. The system can also employ a combustion reactor for forming the water vapor if the initial sample is a hydrocarbon containing sample. Additionally, a second water trap can be provided in the vacuum supply line to the IRMS which removes any residual water vapor that may be desorbed from the Pd filter.

16 Claims, 1 Drawing Sheet

INTERFACE SYSTEM FOR ISOTOPIC ANALYSIS OF HYDROGEN

The present invention was made with support from the United States Government under Grant No. GM49202 awarded by The National Institute of Health (NIH). The U.S. Government has certain rights in the invention.

BACKGROUND OF THE INVENTION

The present invention relates in general to a system for supplying hydrogen gas to an isotope ratio mass spectrometer (IRMS).

High precision hydrogen isotope ratios are conventionally determined in specialized mass spectrometers (IRMSs) which have been available commercially for at least three decades. The IRMS instrument monitors the $HD/H_2$ hydrogen isotope mass/charge ratio signal (m/z=3:2) from a sample and from a standard, and produces isotope ratios of precision to better than 1 part per thousand. Since the hydrogen of interest is not usually in the form of hydrogen gas initially, the common practice is to first convert the hydrogen from its original form (e.g., water) in the sample to hydrogen gas. The methods required for this conversion are exclusively manual in nature and are widely regarded to be difficult, time-consuming, and often do not give satisfactory results. Attempts to automate the conversion for direct introduction into the IRMS, including one commercial attempt set forth in the 1984 paper by William Wong et al., entitled "Evaluation of a Dual Mass Spectrometer System for Rapid Simultaneous Determination of Hydrogen-2/Hydrogen-1 and Oxygen-18/Oxygen-16 Ratios in Aqueous Samples", Analytical Chemistry, 1984, have failed primarily because of water's propensity to linger in vacuum systems and produce "memory effects". Memory effects describe the tendency for hydrogen samples not to be fully eliminated from the measurement instrument prior to introduction of the next sample, thus contaminating the next analysis. This effect is widely known among practitioners in the industry. A significant secondary effect is the problem of fractionation of hydrogen isotopes during transport down gas lines. This phenomenon precludes the use of some strategies to solve the memory effects problem. Until now, no known devices have been available that can convert water to hydrogen gas without memory effects, even though this has been an area of interest since at least the 1950's.

SUMMARY OF THE INVENTION

The present invention seeks to provide an interface system for isotopic analysis of hydrogen which overcomes the long standing memory effect problems that have been associated with prior art systems. This goal is achieved through the use of three key elements; a reduction furnace, a water trap and a Pd filter. The reduction furnace is a microreactor in which a metal, such as Ni, or any other suitable chemically reducing substance is held at an appropriate temperature (approximately 900° C. for Ni) to cause reduction of injected water vapor to hydrogen gas of isotope ratio representative of that in the water. An inert carrier gas is employed to sweep the water vapor into the reduction furnace for this purpose.

After the water is reduced, the inert carrier gas flushes the reacted hydrogen, as well as trace levels of unreacted water, into the water trap for removal of residual water that would foul future analyses. The water trap is preferably any device capable of retaining and/or removing water while passing hydrogen gas, such as a cryogenic trap or a polyfluorinated sulfonated polymer.

From the water trap, the dried stream is directed to the Pd filter which passes hydrogen gas, but not any other gases or substances. Pd and Pd alloys are well known to absorb hydrogen gas, including its isotopes, at room temperature, and to release these gases at elevated temperatures, but do not absorb any other gases. Operating on this principle, the Pd filter comprises a Pd foil that is heated to an appropriate temperature of approximately 330° C., so that it is continuously permeable to hydrogen gases, but is impervious to any other gases. The Pd filter also acts as a barrier from atmospheric pressure to vacuum which is required for the IRMS operation. From the Pd filter, the $H_2$ and HD gases pass into a vacuum line leading to the IRMS inlet.

Although in most instances the Pd filter is necessary for proper operation of the system, the Pd filter can either be eliminated from the system or bypassed as long as the inert carrier gas is not normal He, but is some other gas such as Ar, and the sample gas stream is substantially free from contaminants. Since normal He contains a minor isotope which has the same isotope mass as HD (3), the Pd filter must be employed to filter it from the gas stream prior to entry into the IRMS in order to avoid interference by the He with the HD analysis. If Ar is employed as the carrier gas, however, it does not have to be filtered from the gas stream since it has a different isotope mass than that of HD, and therefore will not interfere with the HD analysis. As a still further alternative, a high resolution mass spectrometer capable of separating HD from $^3$He can be employed with normal He as the carrier gas. In this case, provision must be made for a vent to the atmosphere for excess sample gas flow.

Experimental results have shown that the performance of this combination of elements with respect to memory effects is outstanding. In particular, the results show no memory effect whatsoever in consecutive analyses of samples of deuterium concentration equal to about 887 parts per million, and tap water of deuterium concentration equal to about 147 parts per million. This range is at least four times larger than that of interest for the vast majority of applications.

The system can also be modified for use with other types of hydrogen containing samples, such as hydrocarbons, for example. To utilize the system of such samples, a combustion reactor is employed to combust the hydrocarbons, and convert them to water and carbon dioxide. The resulting water vapor is then directed to the reduction reactor as before. A second water trap, such as a cryogenic trap, can also be positioned between the Pd filter and the IRMS valve block if desired to freeze out any small amounts of water that are desorbed from stainless steel tubing which is employed in the Pd filter body.

BRIEF DESCRIPTION OF THE DRAWINGS

The foregoing and other features and advantages of the present invention will become apparent from the following detailed description of a preferred embodiment thereof, taken in conjunction with the accompanying drawings in which.

DETAILED DESCRIPTION OF THE PREFERRED EMBODIMENTS

Figure 1:
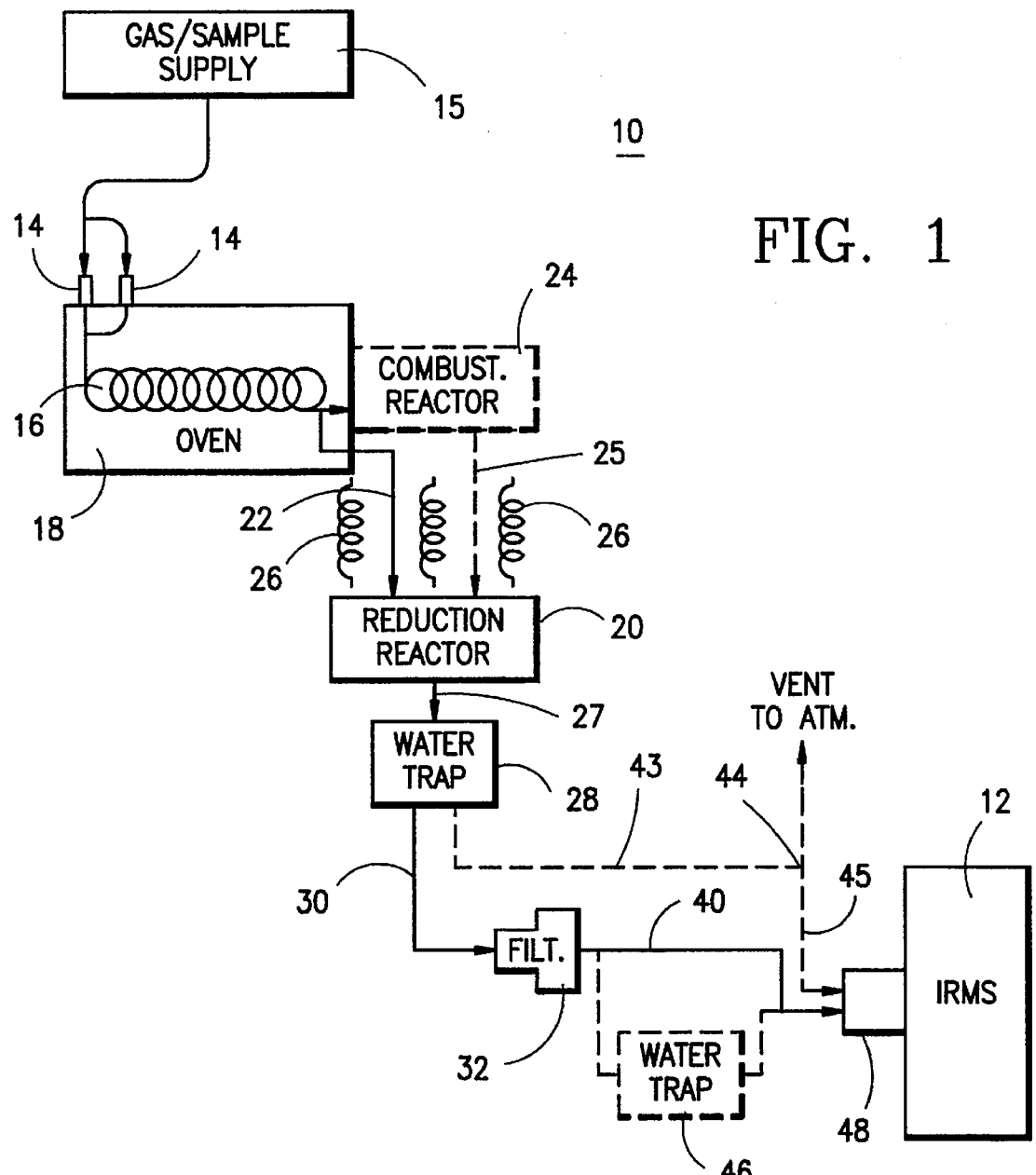
FIG. 1 is a schematic diagram of an interface system constructed in accordance with the preferred embodiment of the invention.

Turning now to a detailed consideration of a preferred embodiment of the present invention, FIG. 1 illustrates a interface system 10 for supplying hydrogen gas to an isotope ratio mass spectrometer (IRMS) 12. The system 10 includes one or more injectors 14 through which a sample to be analyzed is introduced from a gas/sample supply source 15 into a heated transfer line 16 contained within an oven 18. If the sample to be analyzed is water, the oven 18 can be any type of suitable heat source. However, if the sample to be analyzed is one containing a mixture of organic molecules, such as a hydrocarbon sample, then the oven 18 is preferably a gas chromatography oven, and the transfer line 16 is a long coiled tube having an inner coating of chemical material which causes sequential separation of the various organic molecules as they pass through the tube. An inert carrier gas, such as He or Ar, is employed to drive the sample through the injectors 14 into the heated transfer line 16 where the sample is heated and volatilized and/or vaporized by the oven 18.

If the hydrogen containing sample is water, the water vapor that is formed in the oven 18, is swept by the carrier gas directly into a reduction reactor 20 through a transfer line 22. Alternatively, if the hydrogen containing sample is a hydrocarbon, the heated sample is directed from the oven 18 into an optional combustion reactor 24 (represented by dashed lines) where the separated organic molecules in the sample are combusted to form water vapor and carbon dioxide. These gases are then swept into the reduction reactor 20 through a transfer line 25. It should be noted that the transfer line 22 and the optional transfer line 25 must be heated to a temperature in excess of 100° C. to prevent the water vapor in the sample from condensing prior to entering the reduction reactor 20. Any suitable means may be employed for this purpose, such as for example the resistance heating coils schematically illustrated at 26.

In the reduction reactor 20, hydrogen in the water vapor is reduced principally to the chemical forms, $H_2$ and HD. The reactor 20 is preferably a microreactor in which, a metal, such as Ni, Cu, Zn, or U, for example, or any other suitable chemically reducing substance, is maintained at an appropriate elevated temperature (e.g. approximately 900° C. for Ni). If Ni is employed, the Ni chemically reacts with the water vapor and forms the molecules $H_2$ and HD carrying the isotopes hydrogen and deuterium, as well as other reducible elements in the sample. A metal oxide (NiO in the case of Ni) is also formed which remains in the reactor 20.

After the water has been reduced to hydrogen gas of isotope ratio representative of that in the water, the inert carrier gas flushes the reacted hydrogen and trace levels of unreacted water vapor and any contaminants from the reactor 20, through a line 27 into a first water trap 28. The water trap 28 can be any device capable of retaining and/or removing water, while passing hydrogen gas, and for example can be a cryogenic trap or a polyfluorinated sulfonated polymer, such as is manufactured under the trade name Nafion by DuPont. The purpose of the water trap 28 is to remove any residual water in the gas stream exiting the reduction reactor 20 which would foul future analyses. This element therefore acts as the primary means by which "memory effects" are eliminated from the system 10.

Figure 2:
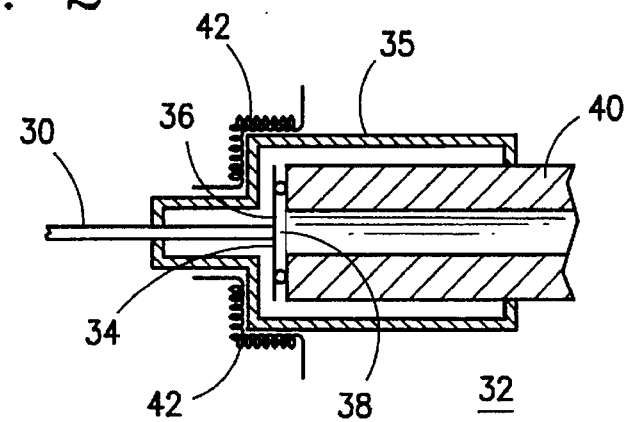
FIG. 2 is a schematic diagram of a Pd filter employed in the system of FIG. 1.

To provide an additional means by which "memory effects" are eliminated from the interface system 10, the hydrogen gas exiting the first water trap 28 is preferably fed through yet another transfer line 30 to a Pd filter 32. The Pd filter 32 is illustrated in greater detail in FIG. 2, and comprises a Pd foil 34 that is contained within a housing 35, and separates an inlet side 36 from a vacuum side 38 of the filter 32. A stainless steel vacuum line 40 contains the hydrogen gas as it exits the Pd filter 32, while the transfer line 30 is held open to the atmosphere. A heating means 42 of any suitable type, such as a resistive heating element, is positioned around the housing 35 for heating the Pd foil 34 to a temperature (approximately 330° C.) at which it becomes permeable to hydrogen gas. It is well known that Pd and its alloys absorb hydrogen gas, including the gas of the hydrogen isotopes, at room temperature, and release these gases at elevated temperatures, but that no other gases are absorbed by these materials. The Pd filter 32, operating with this principle in mind, employs the heated Pd foil 34 as a filter membrane which passes only the hydrogen gas isotopes, and no other gases or materials, such as the inert carrier gas, water vapor or any other contaminants that may be present in the sample. As a result, the Pd filter 32 acts as another means by which "memory effects" are eliminated from the interface system 10.

Although it is preferable and usually necessary to employ the Pd filter 32 in the interface system 10, it is also possible to operate the system without it as long as the inert carrier gas is not He, and the sample gas does not contain excessive amounts of contaminants. If the inert carrier gas is He, the Pd filter 32 is necessary to separate the He from the hydrogen isotopes prior to injection into the IRMS 12. This is necessary because normal He contains an isotope ($^3$He) with the same isotope mass (3) as HD, and would interfere with the HD analysis if it were not removed from the sample. If the Pd filter 32 is not employed, the hydrogen isotopes exit the water trap 28 directly into an optional line 43 (represented by dashed lines) through an open split 44, and then to a vacuum line 45 that is connected to an inlet of the IRMS 12. The open split 44 is required to vent to the atmosphere gas flow in excess of that acceptable by the IRMS 12.

A still further means by which water vapor is prevented from entering the IRMS 12 is a second, optional water trap 46 (also represented by dashed lines) that is employed to freeze out any water vapor that may be desorbed from the stainless steel vacuum line 40 during heating of the Pd foil 34. Stainless steel is known to hold a very small amount of water naturally which is likely to be desorbed during heating. The second water trap 46, which is preferably a cryogenic trap, freezes out this small amount of water from the hydrogen gas stream as it is directed to an inlet of the IRMS 12 comprising a valve block 48. If the second water trap 46 is not employed, the line 40 feeds the sample directly to the IRMS 12 from the Pd filter 32.

In operation of the system 10, the water or hydrocarbon sample is injected with the inert gas carrier into the oven 18 where it is volatilized and/or vaporized. The vaporized sample is then fed directly through the line 22 into the reduction reactor 20 if it is water, or is fed first into the combustion reaction 24 and then into the reduction reactor 20 if it is a combustible hydrocarbon. In the combustion reactor 24, organic samples are combusted to form carbon dioxide and water. In the reduction reactor 20, the water in the sample is chemically reacted to produce the hydrogen isotope gases. From the reduction reactor 20, the separated hydrogen isotope gases, the inert carrier gas and any residual water vapor or other gases, are passed through the first water trap 28 which removes virtually all of the water vapor. Next, the hydrogen isotope gases, the inert carrier gas and any other residual gases are fed to the Pd filter 32 which passes only the hydrogen isotope gases into the vacuum line 40 feeding into the IRMS 12.

In tests of the interface system 10 with water samples, the performance of the system with respect to memory effects has proven to be outstanding. In particular, the results show no memory effects whatsoever in consecutive analyses of samples of deuterium concentration equal to about 887 parts per million followed by tap water of deuterium concentration equal to about 147 parts per million. This is particularly significant since this range is at least four times larger than the range of interest that is used for the vast majority of applications.

In summary, the present invention is the first known interface system for isotopic analysis of hydrogen which is capable of reducing water vapor to hydrogen isotopes, and supplying the hydrogen isotopes to an IRMS with no measurable memory effects. This is particularly significant since memory effects have been a problem in all known prior devices for converting water to hydrogen gas for many years, and until the present invention, no viable solution to this problem had been discovered or devised.

Although the present invention has been disclosed in terms of a preferred embodiment, it will be understood that numerous additional variations and modifications could be made thereto without departing from the scope of the invention as defined by the following claims.

What is claimed is:

1. An interface system for supplying hydrogen isotopes to an isotope ratio mass spectrometer comprising:
   a) a reduction reactor for separating hydrogen isotopes from water vapor, said reduction reactor including an inlet connected to a source of water vapor and an outlet;
   b) a first water trap for separating water vapor from a gas stream exiting said reduction reactor, said water trap including an inlet connected to the outlet of said reduction reactor, and also including an outlet;
   c) a Pd filter comprising a heated Pd foil membrane which is permeable only to hydrogen isotope gases, said Pd filter further including an inlet connected to the outlet of said water trap, and an outlet; and
   d) a vacuum line which is maintained at subatmospheric pressure, and is connected at a first end to said Pd filter outlet, and includes a second end for connection to a sample inlet of an isotope ratio mass spectrometer.

2. The system of claim 1, wherein said reduction reactor contains an element which, when heated, chemically reacts with water vapor to separate hydrogen isotopes from the water vapor.

3. The system of claim 2, wherein said element is a metal.

4. The system of claim 3, wherein said element is Ni.

5. The system of claim 1, wherein said first water trap is a cryogenic trap.

6. The system of claim 1, wherein said water trap is a polyfluorinated sulfonated polymer.

7. The system of claim 1, further including a second water trap disposed in said vacuum line for removing any water vapor that is desorbed from said Pd filter.

8. The system of claim 1, further including an inert gas supply for driving a sample through said reduction reactor and said first water trap to said Pd filter.

9. The system of claim 1, further comprising a heating element for vaporizing a water containing sample before it is supplied to the inlet of said reduction reactor.

10. The system of claim 9, further comprising a combustion reactor positioned between said heating element and said reduction reactor for combusting a hydrocarbon containing sample and thereby forming water vapor and carbon dioxide, said combustion reactor having an outlet connected to the inlet of said reduction reactor for feeding water vapor and carbon dioxide to said reduction reactor.

11. The system of claim 1, further comprising a combustion reactor for combusting a hydrocarbon containing sample, and thereby forming water vapor and carbon dioxide, said combustion reactor having an outlet connected to the inlet of said reduction reactor for feeding water vapor and carbon dioxide to said reduction reactor.

12. A method for forming and supplying hydrogen isotope samples to an isotope ratio mass spectrometer comprising the steps of:
   a) supplying a water vapor containing sample to a reduction reactor for separating hydrogen isotopes from said sample and thereby generating a hydrogen isotope containing sample;
   b) passing said hydrogen isotope containing sample through a first water trap for separating water vapor from said hydrogen isotope containing sample;
   c) passing said hydrogen isotope containing sample from said water trap through a Pd filter comprising a heated Pd foil membrane which is permeable only to hydrogen isotope gases, and thereby generating a hydrogen isotope gas sample; and
   d) passing said hydrogen isotope gas sample from said filter through a vacuum line to a sample inlet of an isotope ratio mass spectrometer.

13. The method of claim 12, wherein said step of supplying said water vapor containing sample to a reduction reactor further comprises heating an element contained within said reduction reactor which chemically reacts with said water vapor containing sample to separate hydrogen isotopes therefrom.

14. The method of claim 12, wherein said step of providing a water vapor containing sample further comprises heating a water containing sample to vaporize the water contained therein.

15. The method of claim 12, wherein said step of providing a water vapor containing sample further comprises:
   1) providing a hydrocarbon containing sample; and
   2) combusting said hydrocarbon containing sample to form a water vapor and carbon dioxide containing sample.

16. The method of claim 12, wherein said step of passing said hydrogen isotope gas sample through a vacuum line further comprises passing said hydrogen isotope gas sample through a vacuum line to a second water trap, and then to said sample inlet of said isotope ratio mass spectrometer.

* * * * *

UNITED STATES PATENT AND TRADEMARK OFFICE
CERTIFICATE OF CORRECTION

PATENT NO. : 5,661,038
DATED : August 26, 1997
INVENTOR(S) : J. THOMAS BRENNA ET AL.

It is certified that error appears in the above-indentified patent and that said Letters Patent is hereby corrected as shown below:

Claim 14, lines 1 and 2 of the claim, column 6, "providing" should read --supplying--.

Claim 15, lines 1 and 2 of the claim, column 6, "providing" should read --supplying--.

Signed and Sealed this

Twenty-fifth Day of November, 1997

*Attest:*

BRUCE LEHMAN

*Attesting Officer*    Commissioner of Patents and Trademarks